(12) United States Patent  (10) Patent No.: US 7,413,563 B2
Corcoran et al.  (45) Date of Patent: Aug. 19, 2008

(54) FLEXIBLE MEDICAL DEVICE

(75) Inventors: Michael P. Corcoran, Woodbury, MN (US); Joseph A. Marino, Apple Valley, MN (US)

(73) Assignee: Cardia, Inc., Burnsville, MN (US)

( * ) Notice: Subject to any disclaimer, the term of this patent is extended or adjusted under 35 U.S.C. 154(b) by 561 days.

(21) Appl. No.: 10/961,244

(22) Filed: Oct. 8, 2004

(65) Prior Publication Data

US 2005/0080400 A1 Apr. 14, 2005

Related U.S. Application Data

(63) Continuation-in-part of application No. 10/445,512, filed on May 27, 2003, now Pat. No. 6,921,397.

(51) Int. Cl.
*A61M 25/00* (2006.01)

(52) U.S. Cl. ..................................... 604/523

(58) Field of Classification Search ......... 604/523–536, 604/264, 96.01, 101.01; 138/155, 100, 120, 138/166

See application file for complete search history.

(56) References Cited

U.S. PATENT DOCUMENTS

| 3,162,214 | A |   | 12/1964 | Bazinet |           |
|-----------|---|---|---------|---------|-----------|
| 4,328,839 | A | * | 5/1982  | Lyons et al. | 138/120 |
| 4,600,037 | A | * | 7/1986  | Hatten  | 138/120   |
| 4,955,384 | A | * | 9/1990  | Taylor et al. | 600/434 |
| 5,381,782 | A |   | 1/1995  | DeLaRama et al. |    |
| 6,273,876 | B1 | * | 8/2001 | Klima et al. | 604/264 |
| 6,682,493 | B2 | * | 1/2004 | Mirigian | 600/585 |
| 6,921,397 | B2 | * | 7/2005 | Corcoran et al. | 604/535 |

* cited by examiner

*Primary Examiner*—Manuel A Mendez
(74) *Attorney, Agent, or Firm*—Kinney & Lange, P.A.

(57) ABSTRACT

This invention relates to flexible medical device. The flexible medical device may comprise interlocking portions formed of a continuous channel. When formed of a continuous channel, the medical device comprises interconnected interlocking portions, rather than independent interlocking portions. The flexible medical device may also be designed so that different portions of the device have different flexibility characteristics.

21 Claims, 14 Drawing Sheets

FLEXIBLE MEDICAL DEVICE

CROSS-REFERENCE TO RELATED APPLICATION(S)

This application is a Continuation-in-Part of U.S. patent application Ser. No. 10/445,512, entitled "Flexible Delivery Device," filed on May 27, 2003.

BACKGROUND OF THE INVENTION

This invention relates to a flexible center connection for use in an occlusion device, and more specifically to a center connection having a flexible section formed of interlocking segments. The flexible section gives the center connection improved torque and flexure characteristics.

Catheters, catheter guide wires, and flexible delivery devices have been used for several years to reach and provide treatment at target locations within the human body. For example, occlusion devices that seal heart defects are delivered to the treatment site via catheter, and balloon angioplasty is performed via catheter. Many designs for catheters and guide wires exist. The most important features of a catheter, guide wire, or delivery device are flexibility, so that it can navigate the winding human vasculature, and torque, so a physician can exert force sufficient to steer the device. Most catheters are made of flexible plastic tubing and come in a variety of lengths and diameters. Most guide wires consist of a metal outer tube comprised of a metal coil coupled with an inner wire.

In practice, physicians generally use a guide wire to reach the desired location in the body. Upon insertion, the guide wire is tracked with either X-ray technology or ultrasound as the physician maneuvers it to the target location within the patient's body. A catheter can then be advanced over the guide wire after the guide wire has reached the treatment site. The guide wire may be left in place or removed while treatment is accomplished via the catheter.

When the physician navigates to the treatment site, the guide wire must have sufficient flexibility to accomplish the sharp and numerous turns in the body's vasculature. If, however, the guide wire is too flexible, the resistance caused by surface contact with the body's vasculature and the numerous sharp turns will cause the guide wire to buckle and the physician will be unable to reach the treatment site. If the guide wire is too stiff, it will not be able to withstand the demanding angles of the vasculature and likewise will not be able to reach the treatment site. Thus there is a need in the art for a delivery tool that possesses both flexibility and navigability.

In addition to the need for delivery tools that possess both flexibility and navigability, other medical devices may be required to be flexible and able to be moved through small diameter catheters. For instance, occlusion devices may be used to repair a wide range of cardiac defects, including patent foramen ovale, patent ductus arteriosus, atrial septal defects, ventricular septal defects, and may occlude other cardiac and non-cardiac apertures. There are currently several types of occlusion devices capable of being inserted via a catheter. The occlusion devices, like the guide wires or catheters, must have sufficient flexibility to accomplish the sharp and numerous turns in the body's vasculature.

Another challenge in deploying an occlusion device in the heart is the variety of the contours of the aperture the occlusion device is meant to close. In particular, when occluding septal defects, the uneven topography in the vascular and septal walls of the human heart makes it difficult to design a device that can adapt to such variations. The challenge in designing an occluder which conforms to the uneven topography is compounded by the fact that the contours of each defect in each individual patient are unique. Poor conformation to the defect results in poor seating of the occlusion device across the aperture, which decreases the ability of the device to successfully occlude the aperture.

Lack of conformation to the walls of the heart can place significant amounts of stress on the occlusion device and decrease the useful life of the device. Once deployed, different parts of the occluder may experience more or less stress as a result of the uneven topography. Having any portion of the occlusion device under increased stress is undesireable.

Thus, there is a need in the art for an occlusion device that will occlude cardiac defects and will match the contours of the heart thereby increasing the life of the device and sealing ability while reducing damage to the surrounding tissue.

BRIEF SUMMARY OF THE INVENTION

The present invention is a medical device having improved torque and flexure characteristics. This device uses a series of permanently interlocking portions to provide flexibility, pushability, pullability, and necessary torque characteristics. The interlocking portions may be formed so that the device comprises a plurality of independent segments, or may be formed of a continuous channel so the device has a unitary structure.

The flexibility and manner in which the medical device articulates at the flexible section can be controlled by varying factors used in creating the interlocking portions. For instance, the number of interlocking portions per unit length may be varied, the size of the kerf used to create the interlocking portions may be varied, the thickness of the wall of the tubular member used to create the medical device may be varied, and the number of interlocking elements around the circumference of the interlocking portions may be varied.

DETAILED DESCRIPTION

Figure 1:
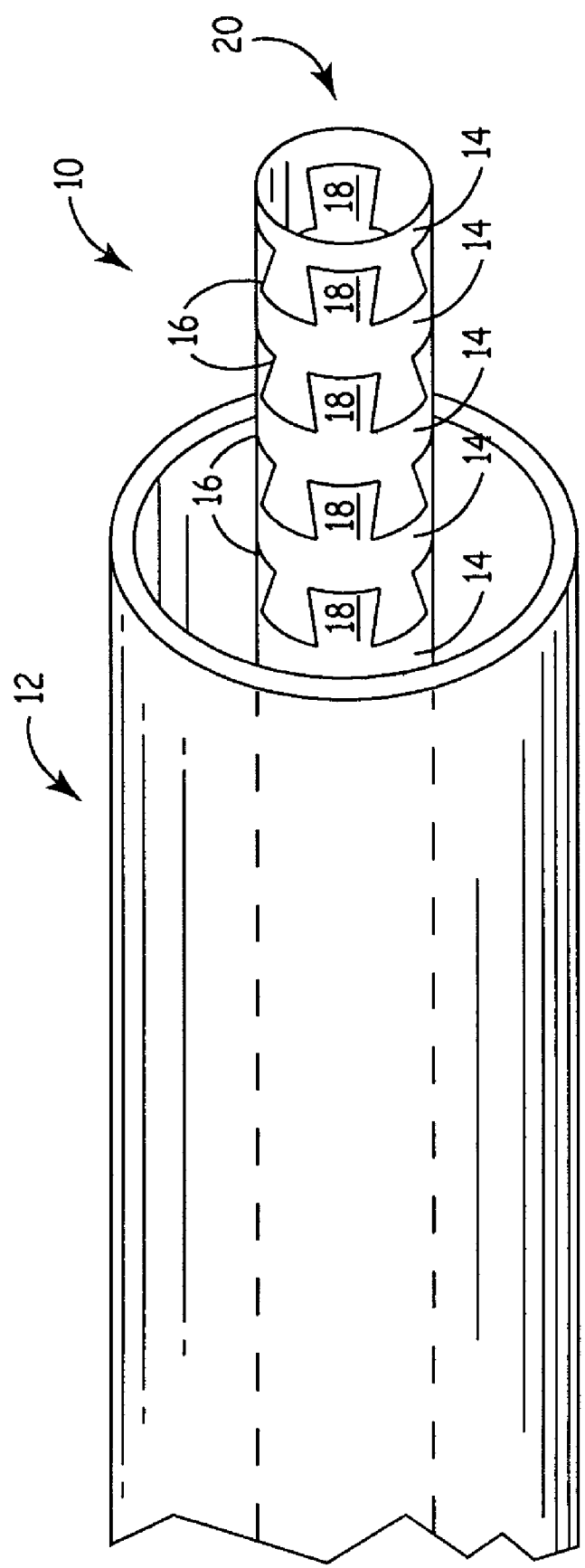
FIG. 1 is a perspective side view of a tubular device extending through a catheter.

FIG. 1 is a perspective side view of a tubular device 10 extending through a catheter 12. The tubular device 10 is comprised of a plurality of interlocking portions 14 separated by channels 16. The interlocking portions 14 comprise a series of dovetail cut interlocking teeth 18 shaped so that the interlocking portions 14 do not disconnect from one another. The interlocking portions 14 are separated by channels 16 which can expand axially to give the device 10 increased flexibility or compress axially for increased rigidity. An end segment 20 terminates the device 10 and may be modified to provide an attachment site for additional devices.

In the embodiment shown in FIG. 1, the delivery device 10 is constructed of a plurality of interlocking portions 14 cut from a single tube. The tube is preferably surgical hypotubing made of stainless steel, titanium, nickel titanium, or another suitable material. The interlocking portions 14 of the delivery device 10 are formed by cutting the tube, either by making a series of cuts in the tube or by making one continuous cut. Depending on the type of cut or cuts made in the tubing, the interlocking portions 14 may be either connected or independent. Independent interlocking portions 14 are more fully described in FIGS. 3-4, while connected interlocking portions 14, formed of a continuous channel, are illustrated in FIG. 6B.

The diameter of the tubing varies depending on the desired end use of the flexible device. In certain circumstances, a tube of tapering or variable diameter may be more effective. For example, if the user prefers that the distal end (the end furthest away from the user) have a very small diameter, the tube may be tapered so that the diameter of the distal end is smaller than that of the proximal end (the end closest to the user). If the device 10 is going to be used in conjunction with a catheter 12, as shown in FIG. 1, the diameter of the device 10 should be similar to the diameter of the catheter 12 so that the device 10 does not have much room to buckle if the device 10 encounters resistance while it is being advanced.

One method of making cuts to form segments 14 is to use a laser. Other suitable cutting methods may also be used to accomplish the cuts, such as using a saw or cutting blade. The method of cutting varies depending on factors such as the size of the tubing and the material used. In an alternate embodiment, the device may be coated with plastic or film when a smooth surface is preferred. The plastic or film must be thin and flexible so that is does not adversely affect the properties of the device 10.

Figure 2:
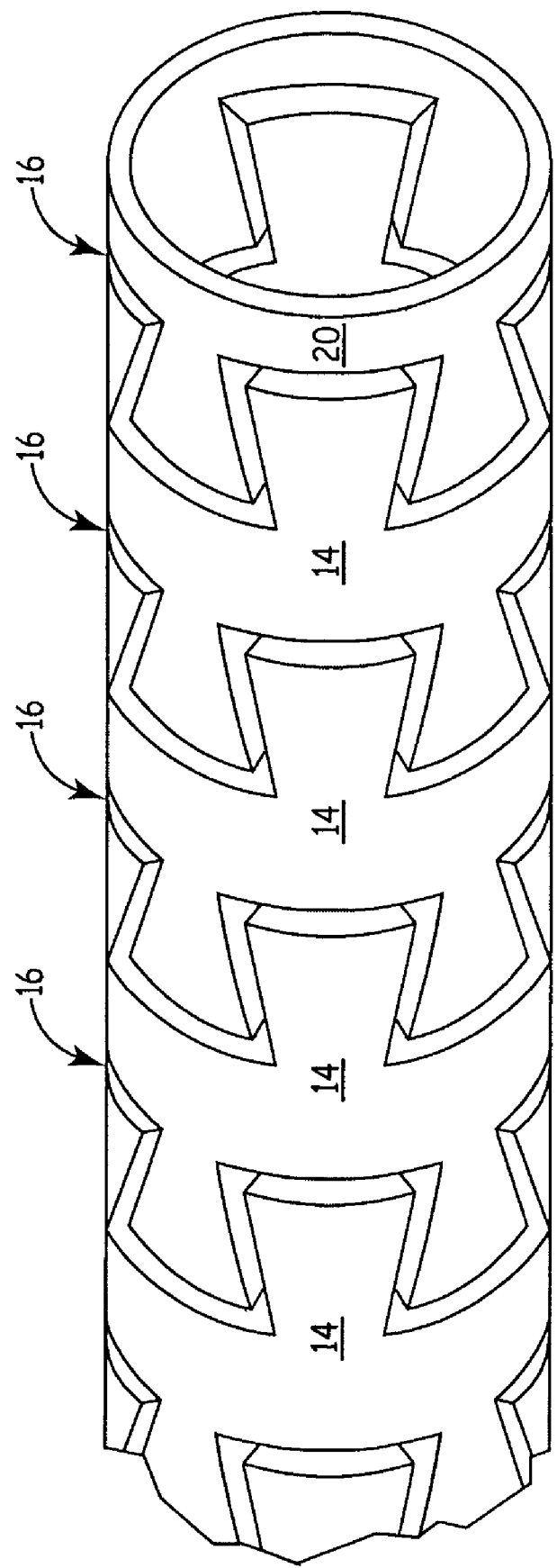
FIG. 2 is a perspective side view of a portion of a tubular device having dovetailed independent interlocking segments.

FIG. 2 further illustrates an embodiment of the present invention formed from a plurality of interlocking portions. Shown in FIG. 2 are interlocking portions 14, channels 16, and the end segment 20. The interlocking portions 14 cannot be axially disconnected because they are defined by a dovetail cut design at each end. The interlocking portions 14 are shaped so that they interlock, or mate, with the adjacent portions, allowing flexure but not axial disconnection. In FIG. 2, a dovetail cut is shown, but the invention is not limited to this pattern. Any pattern of cuts formed in the tubing material may be suitable. Preferably, the pattern of cuts will prevent the portions from axially disconnecting while allowing flexibility along the length of the tubular device.

By cutting the tube into interlocking portions 14 which cannot be axially disconnected because of the cut shape, the portions 14 are able to transmit pushing and pulling forces to adjoining portions 14. The cut design allows the device 10 to transmit axial pushing and pulling forces and also allows transmission of left and right (or counterclockwise and clockwise) twisting forces between interlocking portions 14. In addition, as a result of this design, the amount of rigidity automatically adjusts based on the amount of resistance the device 10 encounters.

When the user pushes on the device 10 at the proximal end, as each interlocking portion 14 experiences the pushing force, the interlocking portion 14 pushes on the distally adjoining interlocking portion 14. Therefore, rigidity is created when the interlocking portions 14 experience pushing or pulling forces because the interlocking portions 14 are locked together with adjoining interlocking portions 14 as the width of the channels 22 decreases. The device 10 becomes more rigid as the channels 16 are compressed because the device 10 becomes more like a solid tube as the interlocking portions 14 interlock. However, when the interlocking portions 14 are not being pushed or pulled or are not experiencing resistance, the channels 16 can expand, the interlocking portions 14 do not lock against each other, and the device 10 is more flexible.

Figure 3:
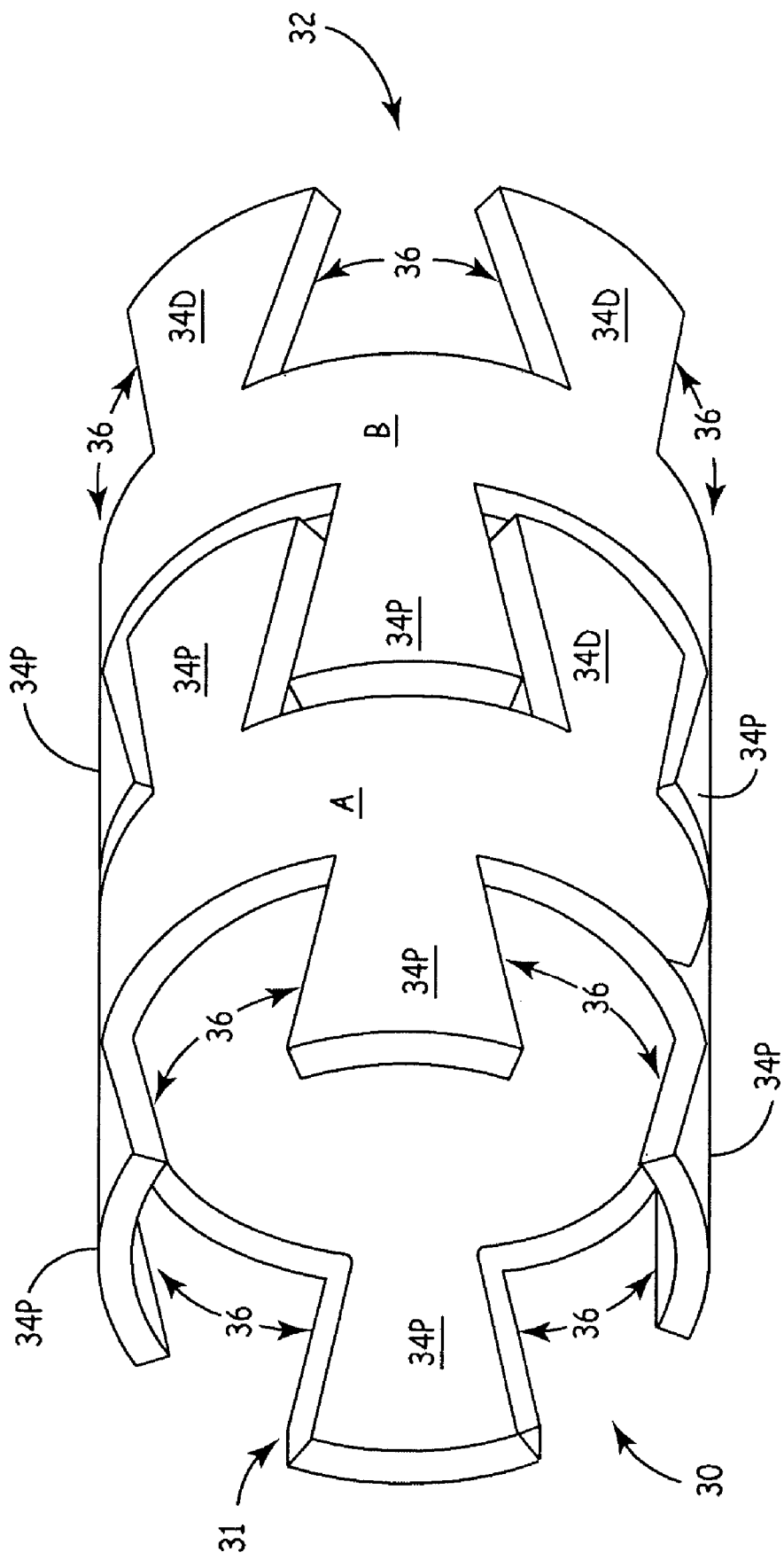
FIG. 3 is a perspective side view of two dovetail cut independent interlocking segments.

FIG. 3 shows an enlarged perspective side view of two independent interlocking portions A, B, each having a proximal end 30 and a distal end 32, as viewed from left to right. The proximal and distal ends 30, 32 are dovetail cut, so that they comprise a plurality of interlocking elements 31. In one embodiment, the interlocking elements 31 comprise proximal and distal teeth 34P, 34D and grooves 36. The grooves 36 are defined by the teeth 34P, 34D. The distal teeth 34D of interlocking portion A fit into the grooves 36 on the adjoining interlocking portion B. The distal teeth 34D of interlocking portion A widen at the ends and therefore cannot be pulled out of the grooves 36 on the adjoining interlocking portion B.

The shape of teeth 34P, 34D and grooves 36 also prevents the interlocking portions A, B from rotating laterally, providing torque when needed. The sides of the teeth 34P, 34D and the sides of the grooves 36 provide additional lateral torsion. Because the interlocking portions A, B cannot rotate laterally, the pushing or pulling force remains longitudinally directed and the device does not "buckle".

In this embodiment, each interlocking portion A, B has four teeth 34D, 34P on each end. If the diameter of the tube used to construct device 10 is increased, the number of teeth 34D, 34P may increase also. Further, as described below, the number of teeth 34D, 34P may be varied based on the amount of flexibility desired. In addition, the angle of the dovetail cut may be varied to alter the flexibility of the device.

Figure 4:
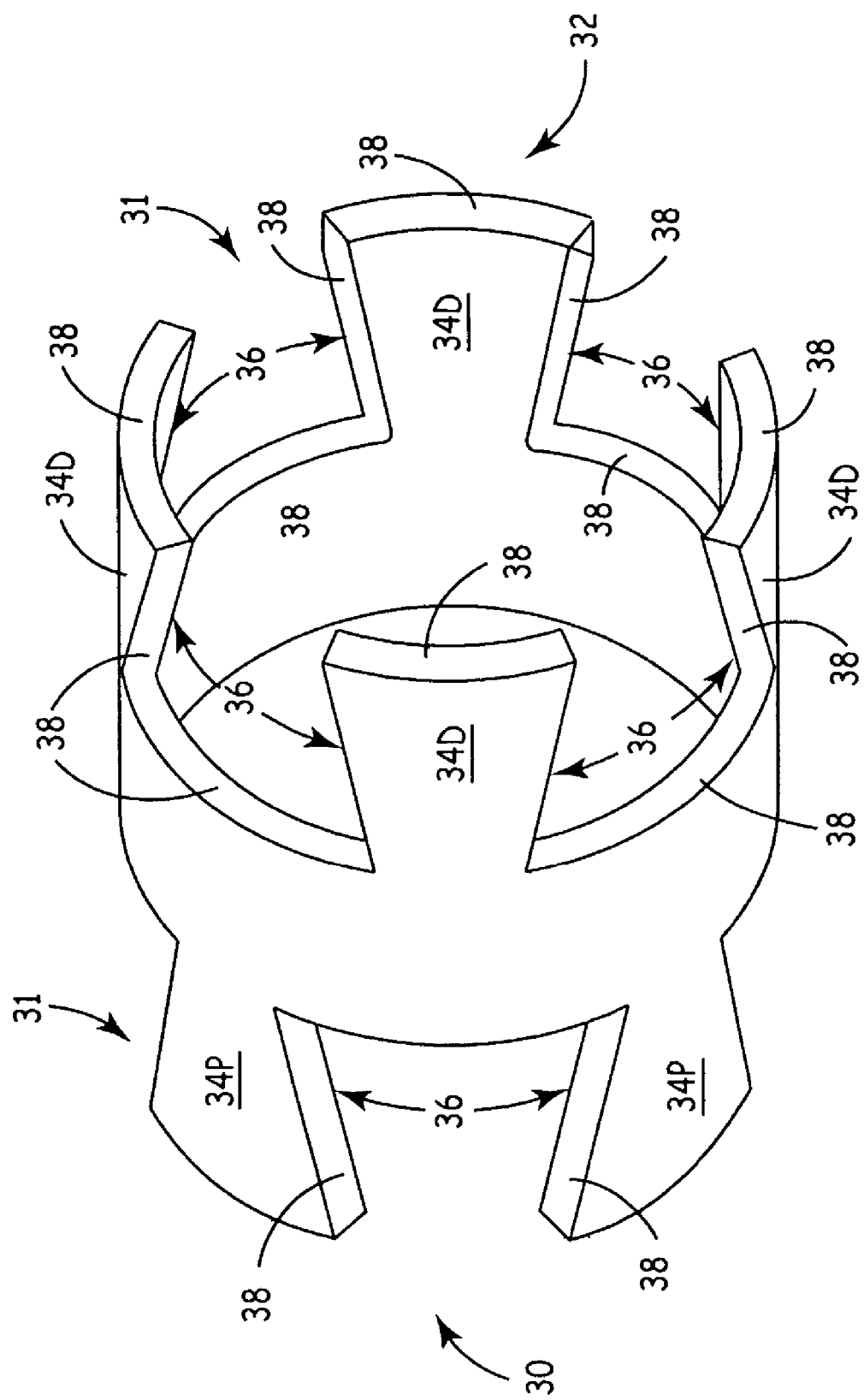
FIG. 4 is a perspective side view of one dovetail cut independent segment.

FIG. 4 is an enlarged perspective view of one interlocking portion A having a proximal end 30 and a distal end 32, as viewed from left to right. Also shown are interlocking elements 31 in the form of proximal and distal teeth 34P, 34D, grooves 36, and mating surface area 38. The teeth 34P, 34D are relatively aligned with the grooves 36 on the opposite end of the interlocking portion A.

By cutting the tube into independent interlocking portions A which cannot be axially disconnected because of the cut shape, the interlocking portions A are able to transmit pushing, pulling, and left and right twisting forces to adjoining interlocking portions 14 through their mating surfaces 38. The thickness of the walls of the tube determines the amount of mating surface area 38 between interlocking portions A. As the mating surface area 38 is increased, the pushing, pulling, and torsional strength is increased. However, the flexibility of the device decreases as the mating surface 38 increases. Thus, the thickness of the walls of the tube may also be varied according to user needs.

FIG. 5A through FIG. 5D are enlarged perspective side views of interlocking elements 31 on interconnecting portions 14 experiencing pushing and pulling forces and left and right twisting forces. FIGS. 5A-5D demonstrate how different sides of the interlocking elements 31 engage different sides of the grooves when the interlocking element experiences either pushing, pulling, or twisting forces. The interlocking elements 31 behave similarly regardless of whether the interlocking portions 14 are independent ring-like segments or are formed as part of a continuous band having a helically arranged cut.

Figure 5B:
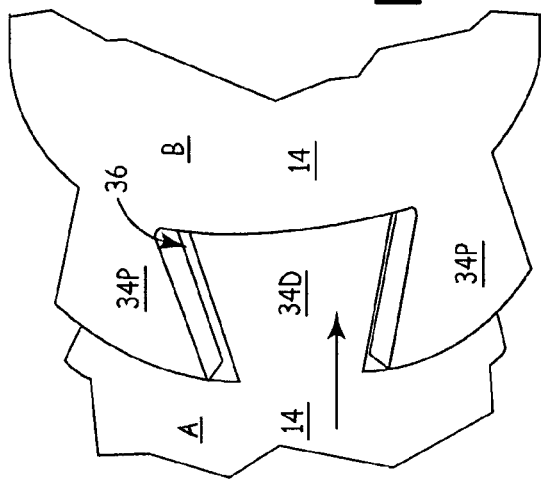
FIGS. 5A-5D are enlarged perspective side views of a tooth of an independent interlocking segment which is experiencing pushing forces, pulling forces and left and right twisting forces, respectively.
Figure 5D:
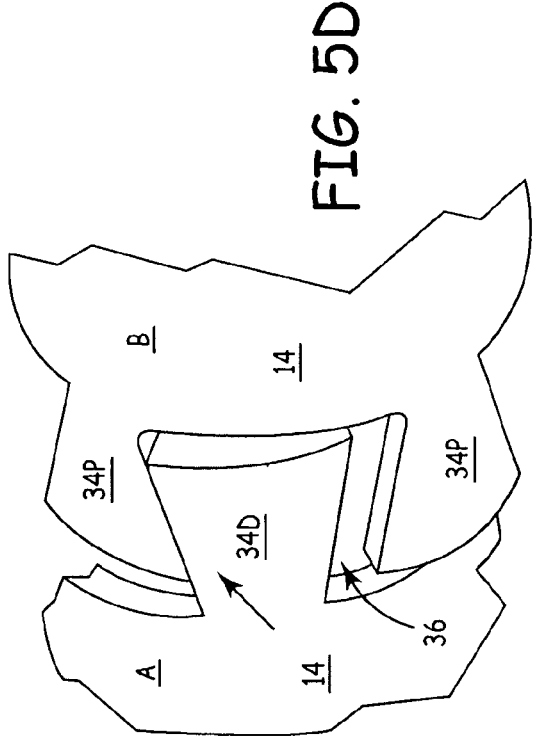
Figure 5A:
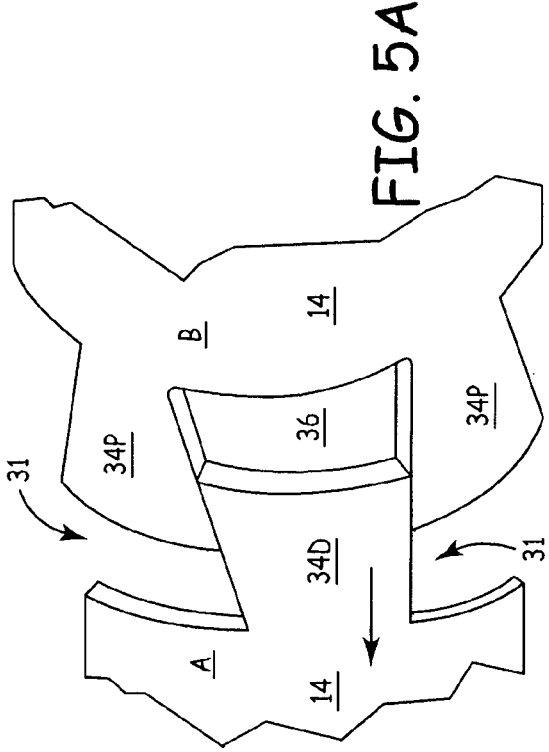

In FIG. 5A, a distal end tooth 34D is located in the groove 36 between two proximal end teeth 34P. Shown are two interlocking portions A, B, a distal end tooth 34D, two proximal end teeth 34P and a groove 36. The distal end tooth 34D is experiencing a pulling force. The distal end tooth 34D cannot be pulled any further out of the groove 36 because the tooth 34D is too wide at its top to be pulled any further. Thus, a jam fit is created and the pulling force experienced by the first interlocking portion A is transferred to the second interlocking portion B.

In FIG. 5B a distal end tooth 34D is located in the groove 36 between two proximal end teeth 34P. Shown are two interlocking portions A, B, a distal end tooth 34D, two proximal end teeth 34P and a groove 36. The distal end tooth 34D is experiencing a pushing force. The distal end tooth 34D cannot be pushed any further into the groove 36 because the tooth 34D has hit the proximal end of the groove 36. Thus, a jam fit is created and the pushing force experienced by the first interlocking portion A is transferred to the second interlocking portion B.

Figure 5C:
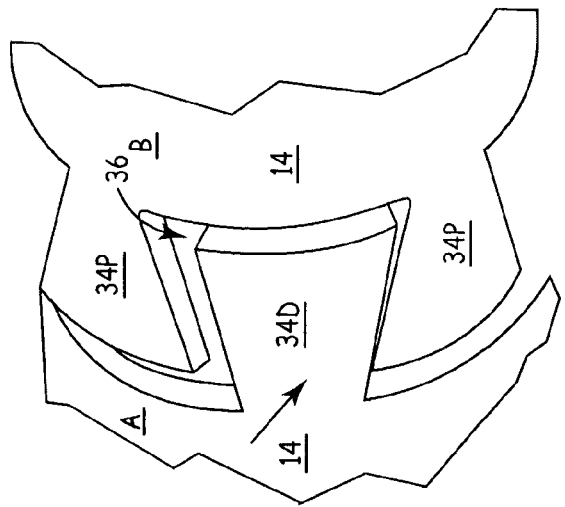

In FIG. 5C a distal end tooth 34D is located in the groove 36 between two proximal end teeth 34P. Shown are two interlocking portions A, B, a distal end tooth 34 D, two proximal end teeth 34 P and a groove 36. The distal end tooth 34D is experiencing a left, or counter-clockwise, twisting force. The distal end tooth 34D cannot be rotated any further in the groove 36 because the tooth 34D has been rotated enough to reach the lower end of the groove 36. Thus, a jam fit is created and the counter-clockwise twisting force experienced by the first interlocking portion A is transferred to the second interlocking portion B.

In FIG. 5C a distal end tooth 34D is located in the groove 36 between two proximal end teeth 34P. Shown are two interlocking portions A, B, a distal end tooth 34 D, two proximal end teeth 34 P and a groove 36. The distal end tooth 34D is experiencing a right, or clockwise, twisting force. The distal end tooth 34D cannot be rotated any further in the groove 36 because the tooth 34D has been rotated enough to reach the upper end of the groove 36. Thus, a jam fit is created and the clockwise twisting force experienced by the first interlocking portion A is transferred to the second interlocking portion B.

Figure 6A:
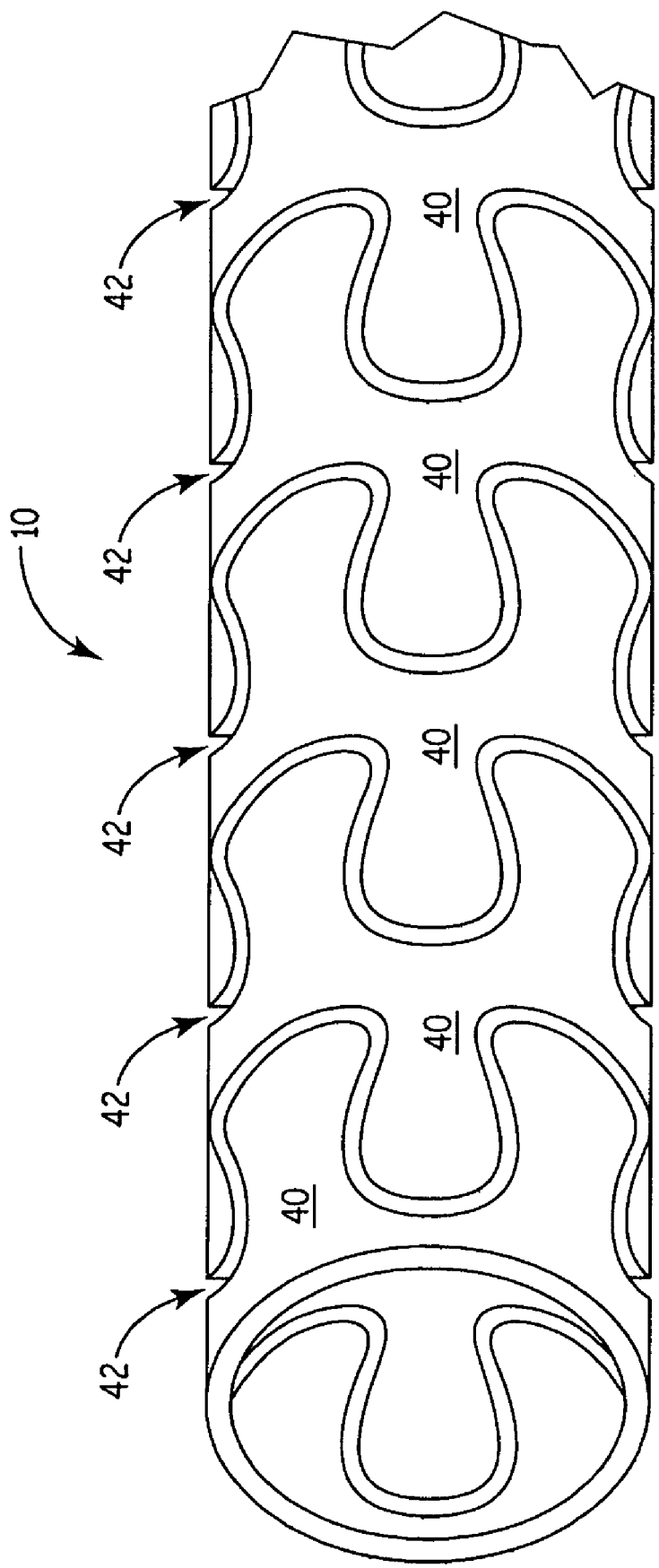
FIG. 6A is a side perspective view of a portion of the tubular device having rounded dovetailed independent interlocking segments.
Figure 6B:
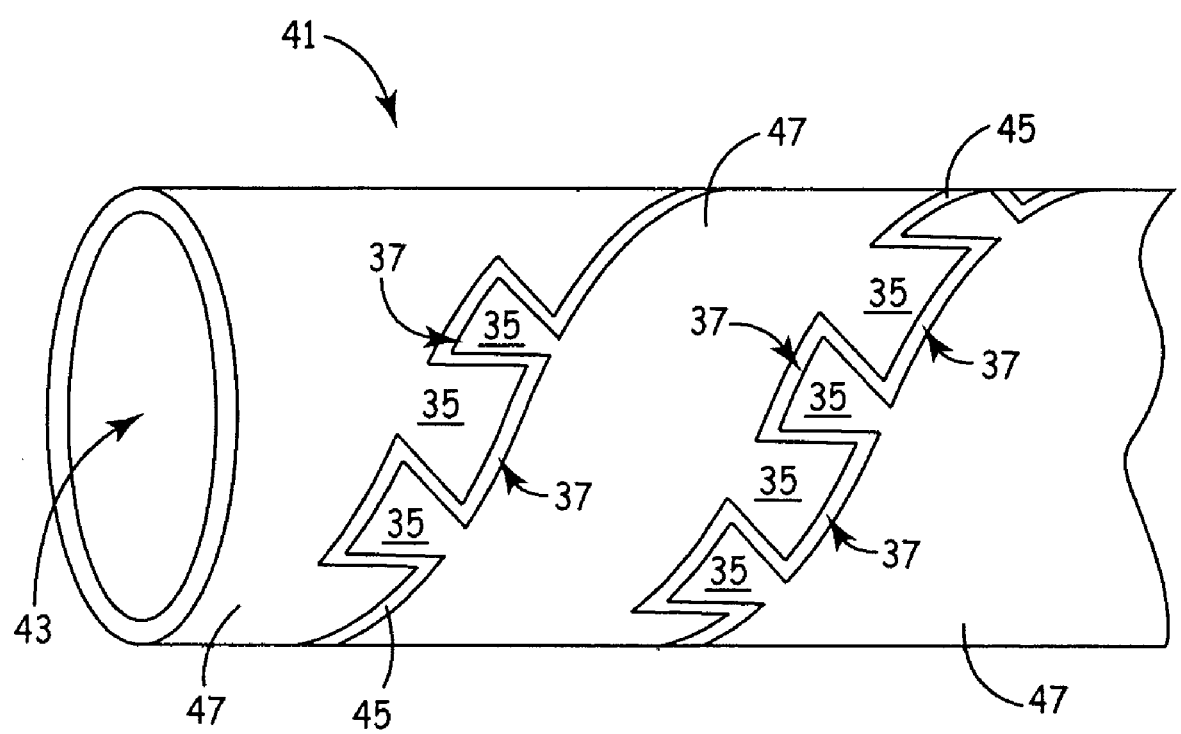
FIG. 6B is a perspective side view of a portion of the tubular device having a continuous channel dividing the tubular device into connected interlocking portions.

FIGS. 6A-6B illustrate alternate cut patterns for forming the device according to the present invention. FIG. 6A is a perspective side view of a portion of a device 10. Shown in FIG. 6A is the device 10 having independent interlocking ring-like portions 40 defined by rounded dovetail cut ends and channels 42. The interlocking ring-like portions 40 remain axially connected because they are defined by a rounded dovetail cut design on each end. The interlocking ring-like portions 40 are shaped so that they interlock, or mate, with the adjacent interlocking portions, allowing flexure but not axial disconnection. Again, the invention is not limited to this cut pattern; any other cut pattern which prevents the interlocking portions from axially disconnecting and allows flexure would work also.

As previously mentioned, by cutting the tube into independent interlocking portions 40 which cannot be axially disconnected because of the cut shape, the interlocking portions 40 are able to transmit pushing and pulling forces to adjoining interlocking portions 40. Rigidity is created when the interlocking portions 40 experience pushing or pulling forces because the interlocking portions 40 lock together with adjoining interlocking portions 40 as the width of the channels 42 decreases. When the interlocking portions 40 are not being pushed or pulled or are not experiencing resistance, the channels 42 expand, the interlocking portions 40 do not lock against each other, and the device 10 is more flexible.

In addition to forming the flexible device 10 illustrated in FIG. 6A of a plurality of independent interlocking rink-like portions, it is also possible to form the flexible device 10 using one continuous cut. When forming the flexible device using a continuous cut, the hollow band forming the flexible device 10 does not comprise independent ring-like portions, but rather remains connected. Further, the invention may comprise a combination of these options, having a portion formed of independent segments, and a portion formed by a continuous cut.

FIG. 6B illustrates one embodiment of forming at least a portion of the flexible device 41 using a single, continuous cut. Shown in FIG. 6B is a portion of a flexible device 41. The flexible device 41 is formed of a tubular member, and thus has a central bore 43. To make the device 41 flex, the device 41 has been cut to form a channel 45 in the device 41.

The channel 45 is formed using one continuous cut, and does not separate the device 41 into independent interlocking ring-like portions. Rather, the channel 45 divides the device 41 into a helical band, which can still be said to comprise interlocking portions 47. One method of forming the channel 45 is to create the channel 45 in a generally helical path along the length of the tube. Possible methods of achieving the helical channel may include rotating the tube during cutting, arranging the cutting mechanism at the appropriate angle, and location relative to the tube or moving the tube in the axial direction during cutting. As a result of the continuous cutting method, the tubular member is not separated into independent portions, but rather the tubular member remains a unitary structure.

Similar to the interlocking elements 31 described in FIGS. 5A-5D above, the channel 45 in the flexible device 41 also creates interlocking elements. In one embodiment, the interlocking elements are teeth 35 which fit into corresponding grooves 37. The shape of the channel 45 ensures that the teeth 35 remain in their corresponding grooves 37, while at the same time the width of the channel 45 results in the flexible device 41 being flexible and able to articulate in a wide variety of directions.

Due to the interlocking elements, the interlocking portions 47 function similarly to independent interlocking portions described above. Rigidity is created when the interlocking portions 47 experience pushing or pulling forces because the interlocking portions 47 lock together with adjoining interlocking portions 47 as the width of the channels 45 decreases. When the interlocking portions 47 are not being pushed or pulled or are not experiencing resistance, the channels 45 expand, the interlocking portions 47 do not lock against each other, and the device is more flexible.

One potential benefit of the device 41 is that rather than being formed of a plurality of independent segments, the device 41 remains a unitary structure due to the manner in which the channel 45 is formed. Because the channel 45 is created by one continuous cut, and no independent segments are formed, the device tends to resist separation.

Once again, the device 41 is not limited to the shape of the channel 45 shown in FIG. 6B. Any continuous cut that forms a channel 45 which creates the desired flexibility and articulation, yet is also capable of transmitting torque, push, and pull forces from one interlocking portion to another, is suitable for use with the present invention. For instance, the dovetail design illustrated in FIG. 6A may also be formed of one continuous cut.

Figure 7:
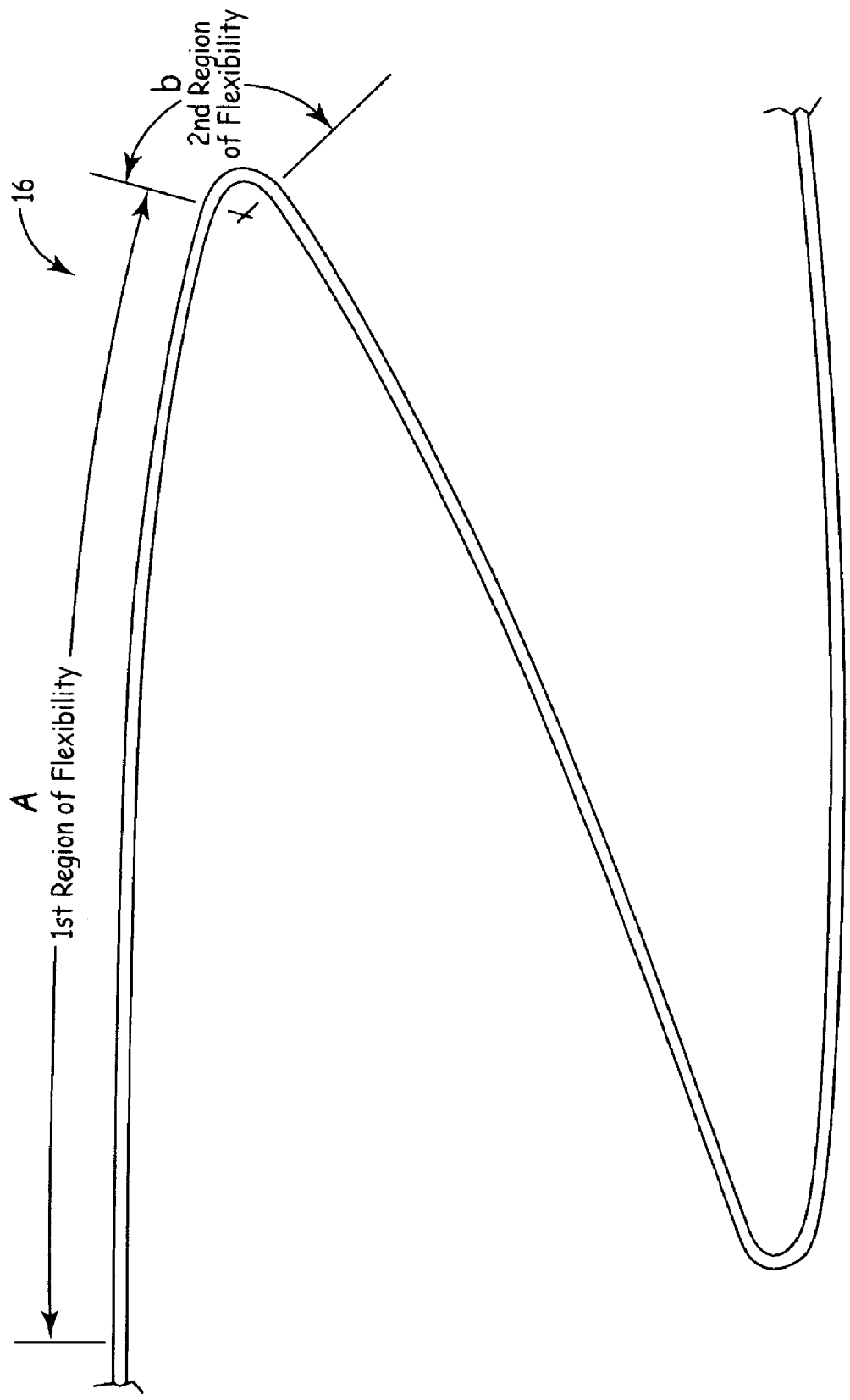
FIG. 7 is a diagram showing how the device is programable along its length.

FIG. 7 is a diagram showing the programmability of the device 10. Shown is the device 10, region R1 and region R2. By varying certain factors, the device 10 can be programmed so that region R1 has a different flexibility and articulation characteristics than region R2. Similarly, by varying certain factors, the stiffness created when pushing and pulling the device, as well as the manner in which the device acts under tension or no tension, can all be controlled. Thus, the device can be programmed to obtain any range of articulation desired.

One method of achieving programmability of the device 10 is to control the number of interlocking portions per unit length. For instance, it is possible to form the cuts so that the number (and thus size) of the interlocking portions vary along the axial direction of the device. In other words, the cuts may be designed so that there are fewer interlocking portions per centimeter. As the number of interlocking portions per centimeter is decreased, the flexibility of the device at that portion will decrease as well. Similarly, as the number of interlocking portions per given length increases, the flexibility of the device 10 at that portion increases. Thus, the number of interlocking portions per given length can be varied to accommodate certain criteria relating to the desired range of flexibility at different locations on the device.

Another example of programming the device 10 is to vary the kerf, the width or thickness of the cut, used to form the channels in the device 10. Increasing the kerf will result in the teeth not fitting as tightly in the corresponding grooves. This looser fit between the interlocking portions increases the flexibility of the device 10. Conversely, decreasing the kerf will result in the device remaining more aligned. A smaller kerf may result in less flexibility, and a more stiff device. Thus, by varying the size of the kerf when forming the device 10, it is possible to program the articulation of the device.

Yet another option for programming the device is to vary the thickness of the material used to make the device. The device is preferably formed of a hollow member. Using a hollow member that has a very thin wall will result in increased flexibility of the device. Conversely, using a material having a thicker wall will result in less articulation. Thus by varying the wall thickness along the length of the device, it is possible to program the articulation of the device 10.

Finally, another method of programming the articulation or flexibility of the device is to vary the teeth and grooves around the circumference of the tubular material. As described above with reference to FIG. 3, the number, size, and shape of the teeth around the circumference of the device can be varied. For instance, increasing the number of teeth around the circumference of the interlocking portions may be used to increase the articulation ability of the device. Similarly, decreasing the number of teeth may decrease the articulation ability of the device.

Any of the above described options may be incorporated when programming the device to achieve different articulation effects in region R1 than those in region R2. In addition, any combination of the above described options may be incorporated into the device to design or program the desired articulation or flexibility of the device. The need to program the device to achieve varying articulation at different areas of the device may be based on a variety of factors.

For example, when a physician attempts to deliver a cardiac occlusion device to the heart via catheter, the end of the delivery device would be very flexible, ideally. Often, the delivery device must be forced into the heart at an angle, which causes the tissue surrounding the defect to become distorted. If the cardiac tissue is distorted, it is difficult to determine whether the device will be properly seated once the delivery device is removed and the tissue returns to its normal state. If the device is not seated properly, blood will continue to flow through the defect and the device may have to be retrieved and re-deployed. In this situation, it is advantageous to have a delivery device that is very flexible at the end that enters the heart. If the end is very flexible, the amount of distortion can be drastically decreased. The amount of articulation available can be increased, using any one or combination of the above described methods, at the distal end of the device 10 to give it the necessary flexibility at the distal end.

The present invention has numerous additional applications. For instance, the invention may be useful in forming a center connection of an occlusion device. Forming a center connection which is highly flexible eases the ability to move the device through a catheter to a location of the aperture to be occluded. Having a flexible section in the center connection of an occlusion device also improves the ability of the occlusion device to fit across a wide variety of apertures in the heart, regardless of the adjacent topography of the tissue or the size or shape of the aperture.

Figure 8:
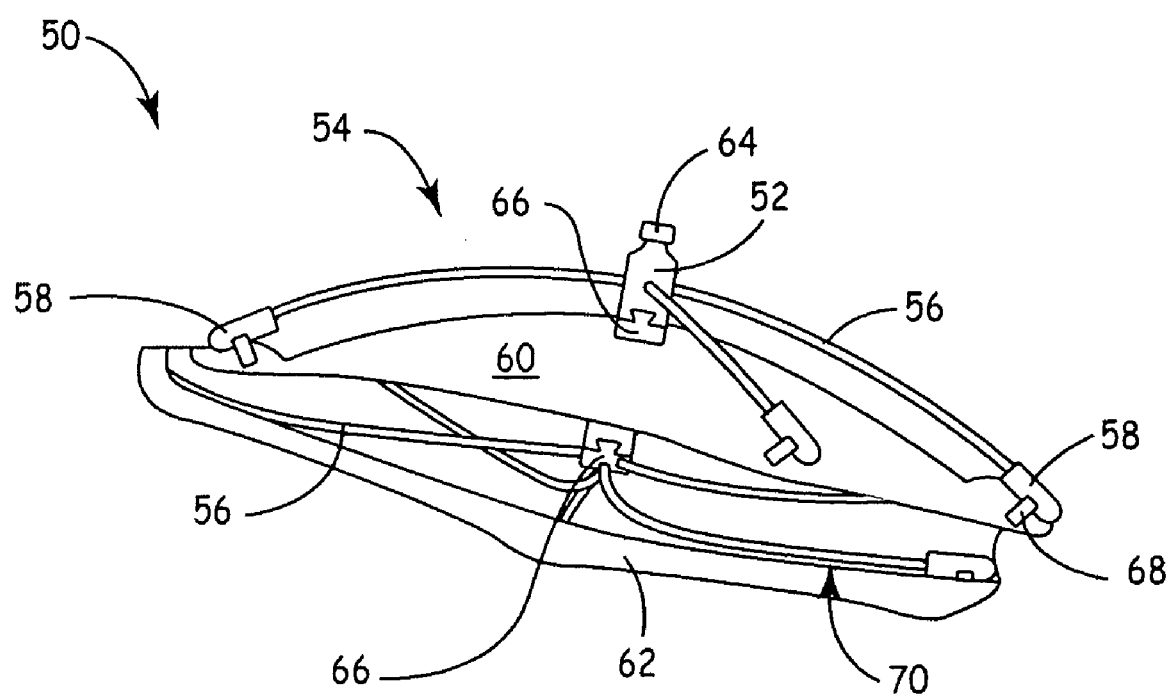
FIG. 8 is a perspective view of an occlusion device with a flexible center connection.

FIG. 8 is a perspective view of an occlusion device 50. The occlusion device 50 comprises a flexible center connection 52, proximal and distal fixation devices 54, 70 (each comprised of six arms 56), atraumatic tips 58, a proximal sheet 60, and a distal sheet 62. The proximal and distal fixation devices 54, 70 are attached to the sheets 60, 62 using any suitable method, such as sutures 68. The arms 56 are connected to the flexible center connection 52 using any suitable method. One method of connecting the arms 56 to the connection 52 is to provide the flexible center connection 52 with drill holes through which the arms 56 extend.

The flexible center connection 52 comprises a flexible portion formed of interlocking portions 66. Overall, the flexible center connection 52 may be any suitable size, but preferably is formed to have a diameter of between about 8 millimeters and about 0.1 millimeters. In addition, the length of the flexible center connection 52 may be any suitable dimension, but is preferably less than about 20 millimeters. The flexible center connection 52 further comprises a knob 64. The knob 64 allows for the device 50 to be grasped as it is inserted into the body through the catheter.

The atraumatic tips 58 are located at the distal end of each arm 56 and serve to minimize damage to the surrounding tissue. The atraumatic tips 58 also provide a place for the sutures 68 to attach the sheets 60, 62 to the proximal and distal fixation devices 54, 70. One method of suturing the sheets 60, 62 to the proximal and distal fixation devices 54, 70 is to provide the atraumatic tips 58 with drill holes through which the sutures 68 pass. In this way, the sheets 60, 62 are sewn to the fixation devices 54, 70 at the atraumatic tips 58. The sheets 60, 62 may also be sutured to the occlusion device 50 along the arms 56.

The occlusion device 50 is constructed so that the proximal and distal fixation devices 54, 70 are easily collapsible about the flexible center connection 52. Due to this construction, the occlusion device 50 can be folded so that the fixation devices 54, 70 are folded in the axial direction. The proximal and distal sheets 60, 62 attached to the proximal and distal fixation devices 54, 70 are flexible, and can likewise collapse as the proximal and distal devices 54, 70 are folded.

Once the device 50 is deployed, the fixation devices 54, 70 serve to hold the proximal and distal sheets 60, 62 in place to seal the defect. To ensure there is sufficient tension to hold the sheets 60, 62 in place, the fixation devices 54, 70 are made of a suitable material capable of shape memory, such as nickel-titanium alloy, commonly called Nitinol. Nitinol is preferably used because it is commercially available, very elastic, non-corrosive and has a fatigue life greater than that of stainless steel. To further ensure that the fixation devices 54, 70 do not suffer from fatigue failures, one embodiment of the present invention relies on making the wire fixation devices 54, 70 of stranded wire or cables.

The sheets 60, 62 are comprised of a medical grade polymer in the form of film, foam, gel, or a combination thereof. One suitable material is DACRON®. More preferably, a high density polyvinyl alcohol (PVA) foam is used, such as that offered under the trademark IVALON®. To minimize the chance of the occlusion device 50 causing a blood clot, the foam sheets 60, 62 may be treated with a thrombosis inhibiting material. One such suitable material is heparin.

The size of the sheets 60, 62 may vary to accommodate various sizes of defects. When measured diagonally, the size of the sheets 60, 62 may range from about 15 millimeters to about 45 millimeters. In some instances, it may be desirable to form the sheets 60, 62 so that they are not both the same size. For instance, one sheet and its associated fixation device can be made smaller (25 millimeters) than the corresponding sheet and its associated fixation device (30 millimeters). This is particularly useful in situations where the occlusion device 50 is to be placed at a location in the heart which is close to other nearby cardiac structures. Making the sheets 60, 62 different sizes may assist in providing optimal occlusion of a defect, without affecting other structures of the heart which may be nearby.

Figure 9:
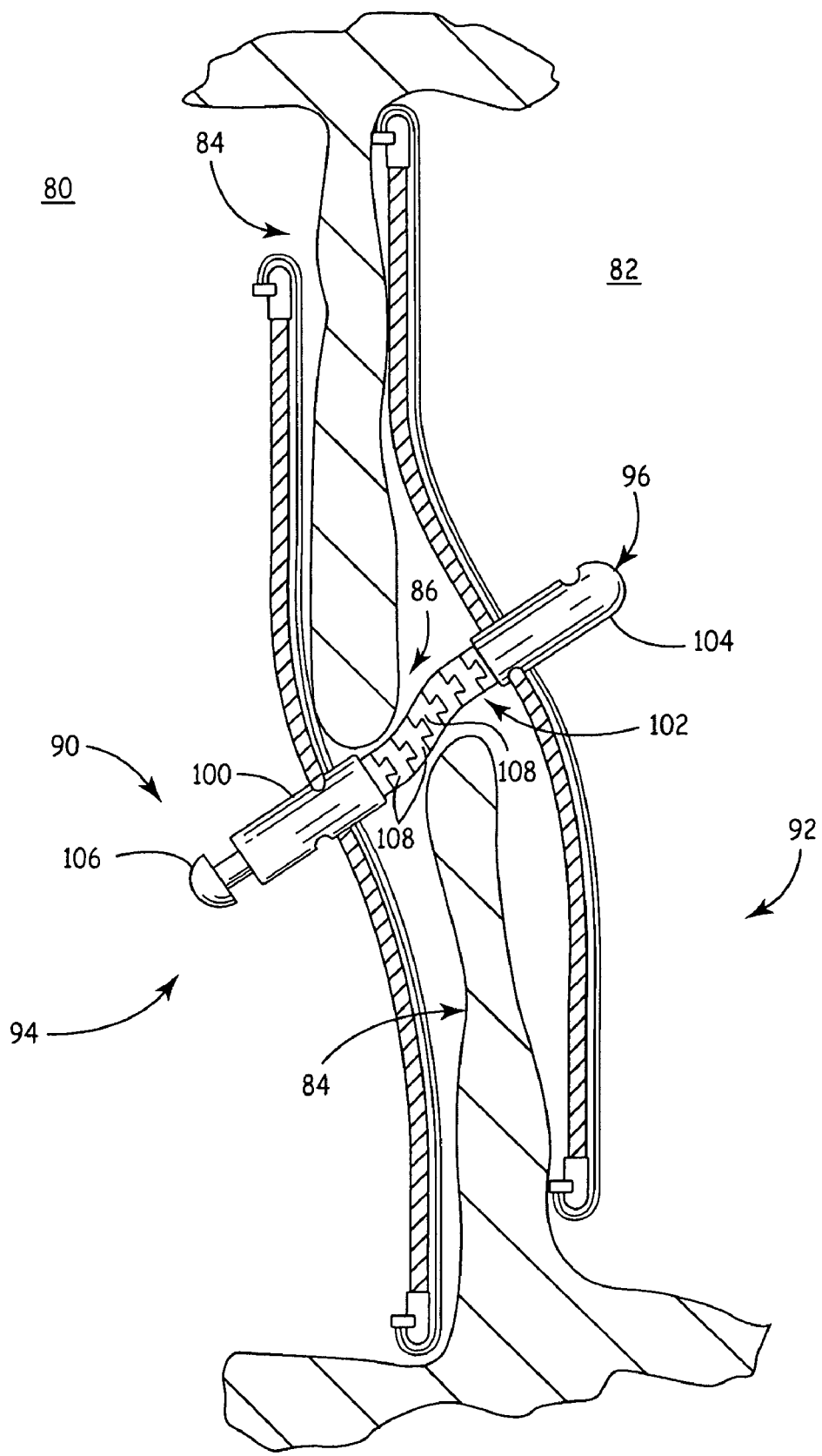
FIG. 9 is diagrammatic view of an occlusion device having a flexible center connection inserted in a defect.

FIG. 9 is diagrammatic view of an occlusion device 90 inserted in a cardiac defect more clearly illustrating a flexible center connection 96. FIG. 9 illustrates a portion of a heart, including a portion of the right atrium 80, a portion of the left atrium 82, and a portion of the atrial septal wall 84. A defect 86 is present in the septal wall 84 in the form of an aperture between the right and left atria 80, 82. This atrial septal defect 86 is one example of a cardiac defect that may be occluded using the occlusion device 90.

As viewed in FIG. 9, the occlusion device 90 comprises a distal side 92, a proximal side 94, and a center connection 96. The center connection 96 of the occlusion device 90 comprises a proximal end cap 100, a flexible center section 102, and a distal end cap 104. The distal side 92 comprises an occluding sheet 91 and fixation device 93 in the form of stranded wire arms 93. Similarly, the proximal side 94 comprises an occluding sheet 95 and fixation device 97 in the form of stranded wire arms 97. For simplicity, the occlusion device 90 is shown with only one set of arms 93 on the distal side, and one set of arms 97 on the proximal side. The proximal end cap 100 further comprises a grasping knob 106 for grasping the occluder 90, such as by a delivery forceps, during movement through a delivery device and subsequent deployment at the defect 86.

The flexible center section 102 of the center connection 96 comprises several interlocking portions 108, similar to those described above with reference to the delivery device in FIG. 1. By forming at least a portion of the center connection 96 to include a flexible section 102, the center connection 96 improves the seating ability of the occlusion device 90 without sacrificing any strength for the occlusion device 90 to properly occlude the defect, or functionality (i.e. ability to move through a catheter, to twist or turn during deployment, to place against a septal wall) needed to properly deploy the occlusion device 90.

Further, though the center connection 96 contains a flexible section 102, the flexible section 102 has no negative effect on the ability to move the occlusion device 90 through a catheter. As described above, rigidity is created when the interlocking portions 108 experience pushing or pulling forces because the interlocking portions 108 lock together with adjoining interlocking portions 108. As such, the flexible section 102 can be made to be sufficiently rigid when so required, such as when the two end sections 100, 104 are pushed toward one another when the occlusion device is moved through a catheter.

At the same time, the flexible section 102 can be made to be flexible when so desired. When the interlocking portions 108 are not being pushed or pulled or are not experiencing resistance, the interlocking portions 108 do not lock against each other, and the center section 102 is more flexible. This flexibility of the section 102 allows for the device to be moved easily through sharp turns in a catheter, and allows for the device to be placed so that one side of the device is easily articulated relative to the other side of the device.

Further, once deployed, the interlocking portions 108 are strong enough to properly hold the two sides 92, 94 of the occlusion device 90 properly in place. Thus, the flexible section 102 of the center connection 96 provides the functionality required to deploy the occlusion device, while offering the benefits of a fully articulating center connection.

As FIG. 9 demonstrates, an occlusion device 90 having a flexible center connection 96 is capable of conforming to an irregularly shaped defect 86. More specifically, an advantage of the present invention is that the flexible center connection 96 allows the distal and proximal sides 54, 56 to conform more readily to the contours of the heart after it is deployed, providing a custom fit to a variety of defects. Often, when implanted, an occlusion device 90 is located in an irregularly shaped defect 86. Having a flexible center section 102 allows the occlusion device 90 to fit in a wider variety of defects, despite the shape or size of the defect.

For instance, as viewed in FIG. 9, the septal wall 84 on the bottom of the defect may have a different shape and thickness than the top of the defect. In such cases, one or more arms 93, 97 on one side of the occluding device 90 may be bent open further than the arms 93, 97 on the other side. Any time the occluding device 90 is positioned so that any of the arms 93, 97 are deformed from their desired end shape, that portion of the occlusion device 90 carries a high static load which both increases pressure on the surrounding tissue and increases the possibility of breakage of the device 90. If the center connection 96 is flexible, the center connection 96 can bend such that the arms 93, 97 associated with the proximal and distal sides 92, 94 of the occlusion device 90 seat with a reduced amount of distortion, allowing the device 90 to better conform to the defect. The ability to conform to a variety of heart contours provides better seating, reduces tension (increasing fatigue life), and decreases the likelihood of damage to tissue resulting from breakage and from pressure the device places on surrounding tissue.

The flexible center connection 96 also improves the ability to place the occluder 90 using a delivery device, such as a catheter. If the center section 96 of the occlusion device 10 is rigid, the center connection 96 must enter the defect 86 following the same angle of insertion as the catheter or other delivery device used to deploy the occluder 90. As a result, the insertion angle is limited by the catheter's angle of insertion.

Often, due to limited space, the catheter enters the heart at an angle that is not perpendicular to defects in the septal wall 84. In such situations, the device 90 cannot enter the defect 86 optimally because the line of the center section 96 must follow the same line as the catheter. The device 90 may need to be forced into the defect 86 at an angle, which may cause the tissue surrounding the defect 86 to become distorted. If the surrounding tissue is distorted by the catheter 50, it is difficult to determine whether the device 90 will be properly seated once the catheter 50 is removed and the tissue returns to its normal state. If the device 90 is not seated properly, blood may continue to flow through the defect 86 and the device 90 may have to be retrieved and re-deployed.

When the center connection 96 is articulated or flexible, the insertion angle of the device 90 is not restricted to that of the catheter. Once the distal side 92 of the occlusion device 90 is pushed out the catheter, the flexible section 102 of the center connection 96 allows the occlusion device 90 to be more precisely positioned in the defect. As such, the flexible section 102 allows for an infinite angle of insertion by simply allowing the flexible section 102 to move once the distal side 92 of the occlusion device 90 has been deployed.

This variable insertion angle also allows the device 90 to enter the defect 86 at an optimum angle, minimizing distortion of surrounding cardiac tissue. If the tissue is not distorted when the device 90 is deployed, the seating of the device 90 should not change drastically once the catheter is removed. Because the device 90 can be properly seated at the first insertion, the number of cases that require retrieval and redeployment should decrease.

Figure 10A:
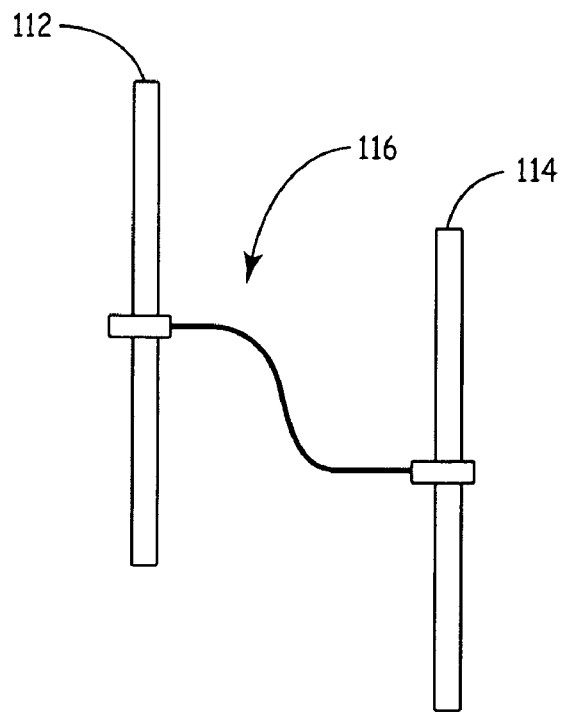
FIGS. 10A-10C are simplified side views of an occlusion device having a flexible center connection.
Figure 10B:
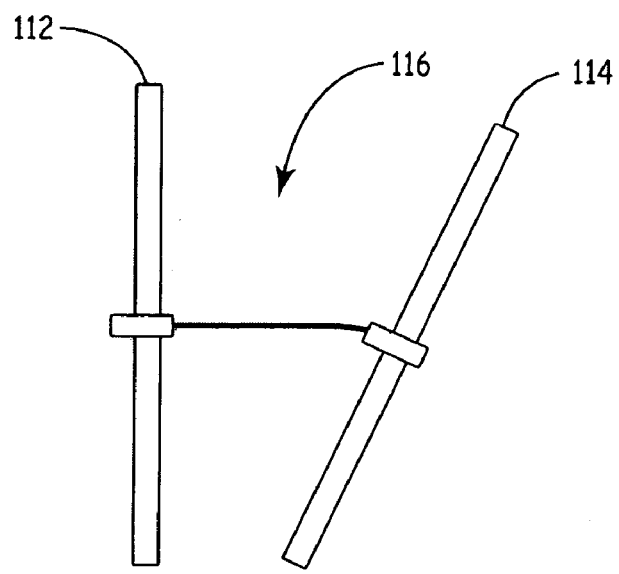
Figure 10C:
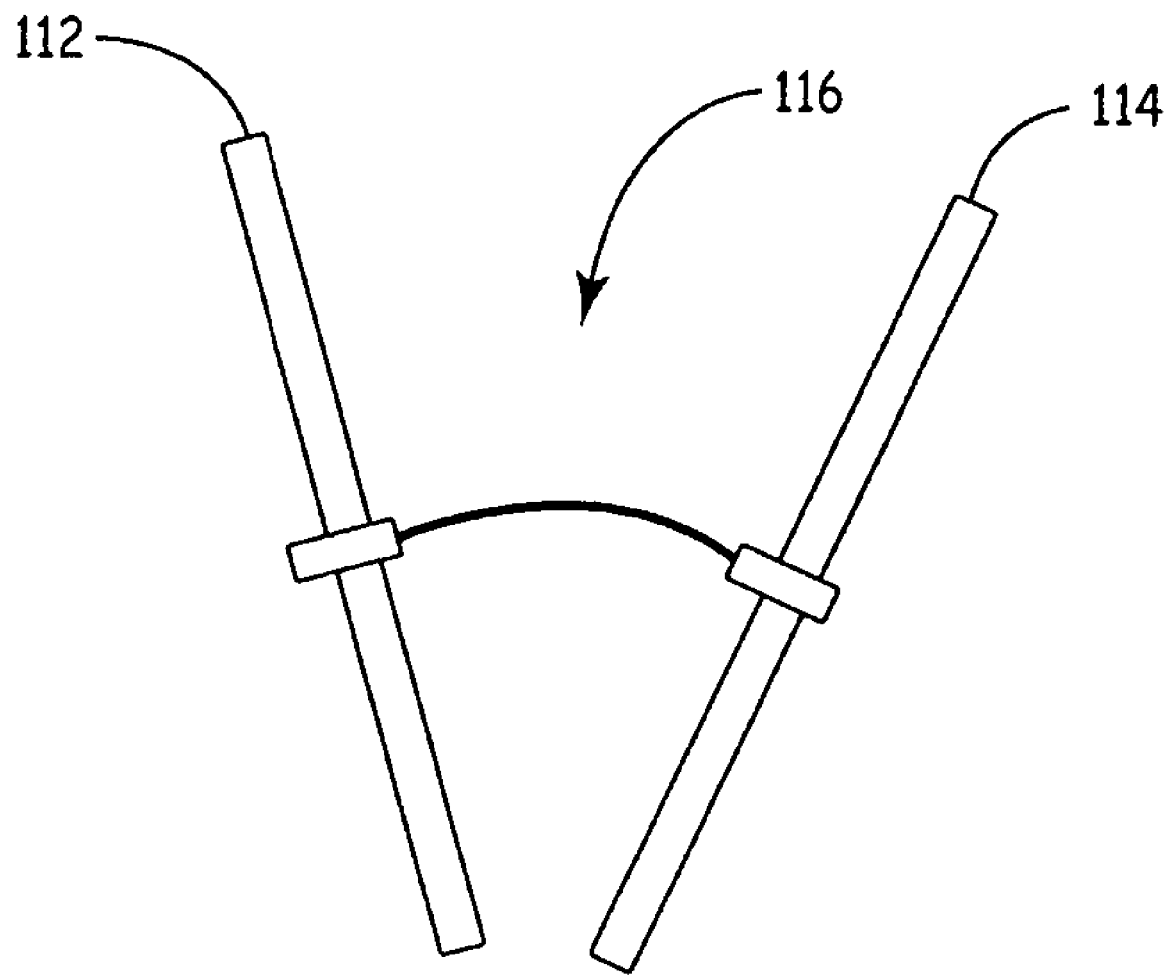

FIGS. 10A-10C illustrate the wide variety of relative positions of the two sides of an occlusion device that are possible when a flexible center connection is used between them. FIG. 10A shows an occlusion device 110 having a first occluding body 112, a second occluding body 114, and a flexible connection 116 connecting the two. While a rigid center would require that both occluding bodies 112, 114 be axially aligned, the flexible connection 116 allows the first occluding body 112 to be offset from the second occluding body 114. As such, the flexible connection 116 does not require one occluding body 112 to be horizontally aligned with the other occluding body 114.

FIG. 10B illustrates yet another range of movement provided by the present invention. FIG. 10B illustrates the occlusion device 110 having the first occluding body 112 connected to the second occluding body 114 using a flexible connection 116. The flexible connection 116 allows for one occluding body 112 to be arranged in a non-parallel configuration relative to the other occluding body 114.

FIG. 10C illustrates yet another range of movement provided by the present invention. As illustrated in FIG. 10C, the flexible center connection makes it possible for one or both sides of the occluding body to articulate. As FIGS. 10A-10C illustrate, the flexible section 116 provides for a near infinite range of movement of one occluding body 112 relative to the other 114.

The flexible section 116 of the occlusion device 110 is formed as a band comprising interlocking elements, such as teeth, as described above. Similar to the medical device described above, the band may be formed into independent ring-like portions which interlock at the interlocking elements. Alternatively, the band may take the form of a helix, with the interlocking elements being formed in a generally helical path along the length of the flexible section 116.

Figure 11:
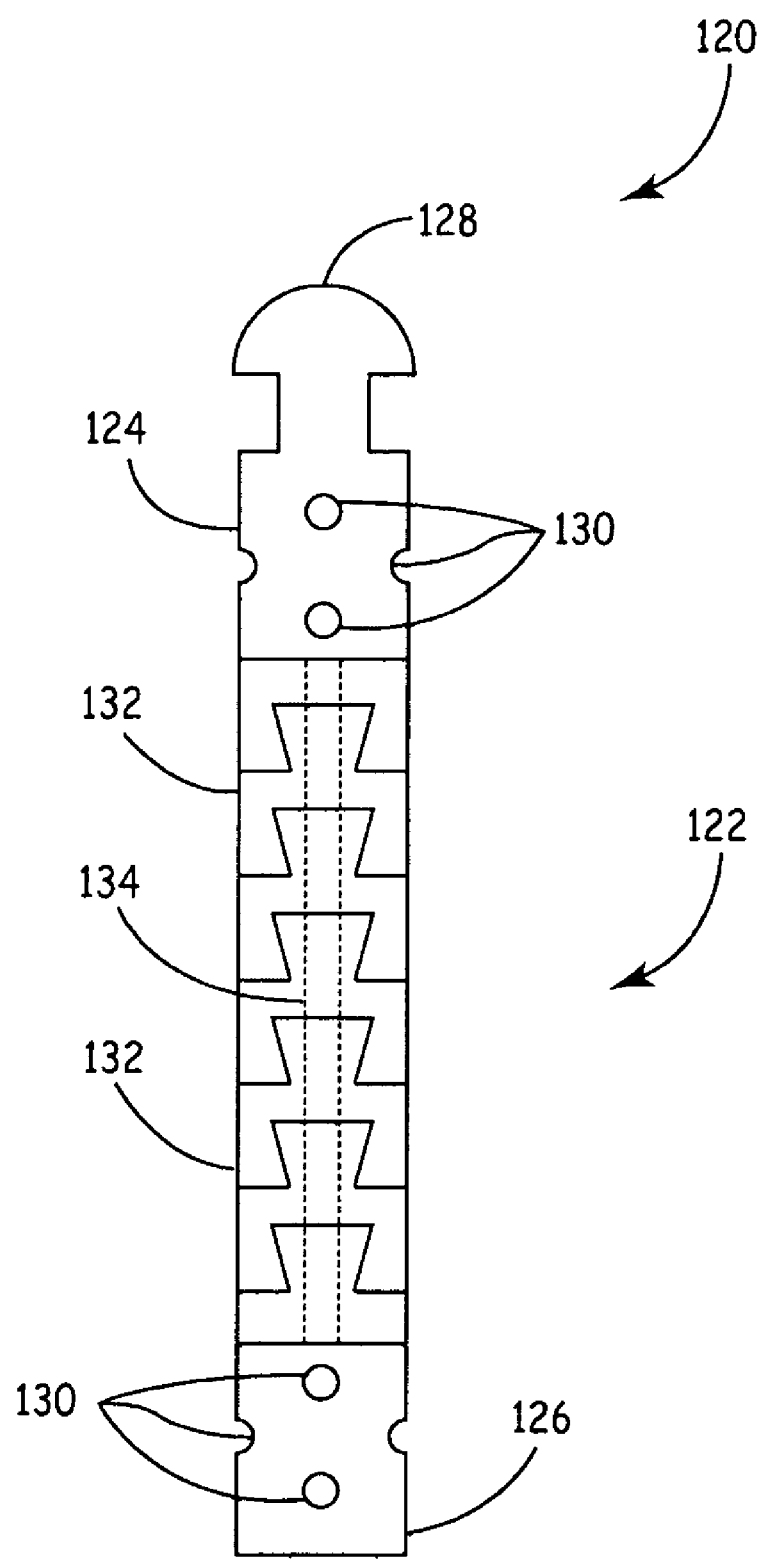
FIG. 11 is a side view of one embodiment of a flexible center connection for use in an occlusion device.

FIG. 11 is a plan view of one embodiment of a center connection 120 having a flexible center section 122. The center connection 120 comprises a first end 124 and a second end 126. The first end 124 has a grasping knob 128, as described above. Also shown on both the first and second end caps 124, 126 are holes 130. The holes 130 provide a location for attaching the occluding bodies, such as the wire fixation devices (FIG. 8) to the center connection 120.

The center section 122 comprises a plurality of interlocking portions 132. A tether 134 extends through the center of the interlocking portions 132. The interlocking portions 132 allow for at least the center section 122 of the center connection 120 to be extremely flexible. At the same time, the manner in which the interlocking portions 132 interlock ensures that the center connection 120 has the required structural strength in the axial direction so that the end caps 124, 126 do not become separated anywhere along the flexible section 122.

The tether 134 may further serve to ensure the structural integrity of the center connection 120. The tether 134 may be used to connect the first end cap 124 to the second end cap 126, and may extend through a hollow middle of the flexible center connection 120. In this way, the tether 134 serves to further ensure the center connection 120 remains connected. Though described in terms of a center connection 120, a tether 134 may be utilized in any variety of medical device utilizing the features of the present invention.

The end caps 124, 126 may be attached to the flexible section 122 in any suitable manner. For instance, the end caps 124, 126 may be formed separately from the flexible center section 122, and crimped together to form the center connection 120. In addition, it may be possible to simply form one or both of the end caps 124, 126 and the flexible center section 122 as a unitary structure. As such, when forming the flexible center section 122, the end caps 124, 126 would be designed so that one side of the end caps 124, 126 provides the location for attaching the occluding bodies, while the opposite side of the end caps 124, 126 is formed to have an interlocking region configured to interlock with an adjacent interlocking portion 132.

Similar to the programmability of the medical device described above with reference to FIG. 7, the flexibility of the center section 122 may be likewise programmable. For instance, the number of cuts per length may be varied along the length of the center section 122 to make certain of the center section 122 more or less flexible. Further, the thickness of the material used to form the flexible center section 122 may be varied, the channel width may be varied, or the number, size, or shape of the teeth may be varied.

Given the manner in which the interlocking segments 132 interlock with each other, the center section 120 is extremely flexible at the center section 122, while retaining the ability to transmit torque, push, and pull forces. In addition to being able to fully articulate, when deploying the occluder, the center connection 120 is also capable of transmitting torque. This ensures that it is possible to rotate the occlusion device, if required, during deployment.

While it may be required to rotate the occlusion device during deployment, it is often not desired for the occluding bodies to be rotatable relative to the center connection or relative to each other. Preventing one occluding body from rotating relative to another is beneficial during deployment to provide a better view, such as by x-ray, of the device after it is deployed. If the occluding bodies are capable of rotating, both occluding bodies may be aligned after deployment, making it difficult for the physician to determine the location of one or both of the occluding bodies across the defect. Further, ensuring the fixation devices of each occluding body are off set from one another improves the seating ability of the device, which in turn improves the occluding ability of the device. As such, the occlusion device may be designed to allow flexibility and torque of the overall device, but minimize rotation of one occluding body relative to the other.

Figure 12:
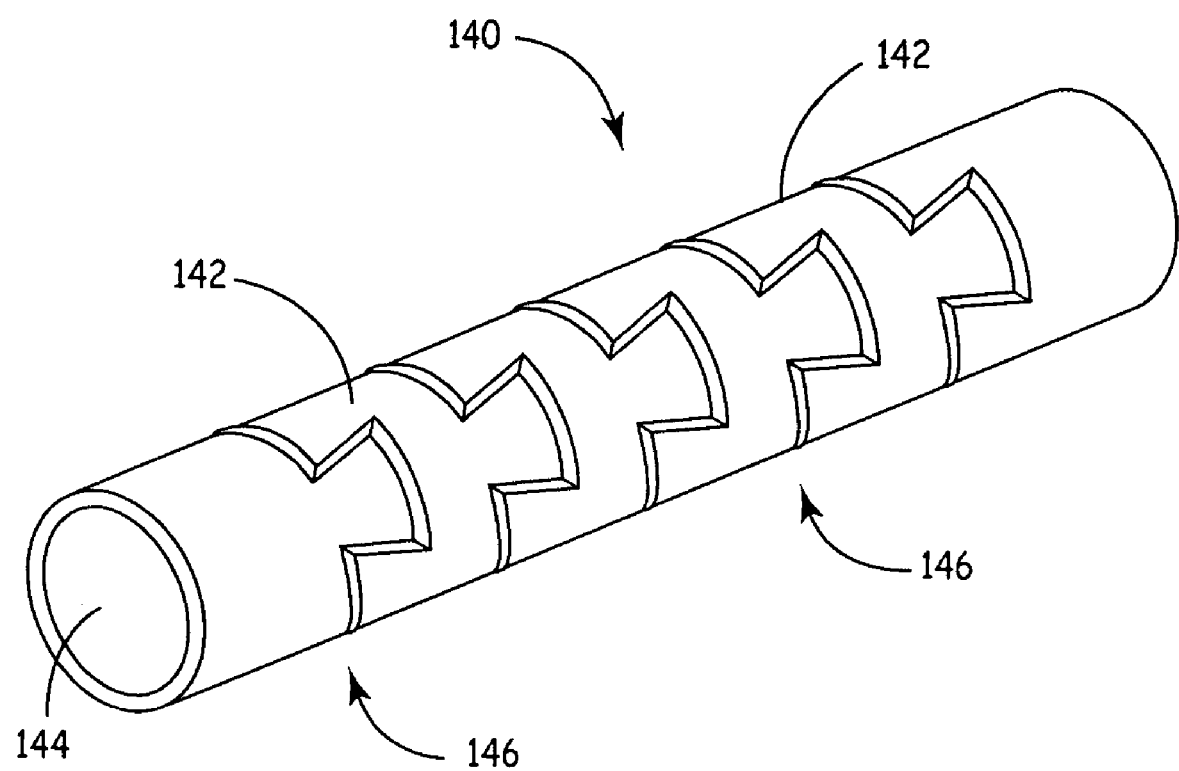
FIG. 12 is a perspective view of one embodiment of a portion of a flexible section for use in a center connection.

FIG. 12 is a perspective view of one embodiment of a flexible center section 140 for use in a flexible center connection. Shown in FIG. 12 are several interlocking portions 142. In forming the flexible center section 140, any suitable material may be used. Further, any suitable method may be used to create the interlocking portions 142. One suitable method is to form the flexible section 140 by making a plurality of cuts in a tube of material, such as a metal.

In FIG. 12, the interlocking portions 142 comprise a center bore 144. The center bore may be necessary when forming the flexible section 140 by making cuts in a metal tube, such as by utilizing a laser cutting device. The size of the bore 144 may vary depending upon the desired structural characteristics of the flexible section 140. Further, the size of the bore 144 may vary depending on the technology used to create the interlocking portions 142.

Similarly, as described above with reference to FIG. 6A-6B, though shown having one particular size and shape of cuts 146, the invention is not so limited. Rather, the cut pattern may be any such cut pattern as provides for the desired flexibility while preventing axial disconnection.

The flexibility, along with the torsional ability of the flexible section 140 is similar to that described above with reference to FIGS. 5A-5D. Further, though described as having a hollow core 144, the invention is not so limited. As long as the interconnecting portions 142 can be formed, the flexible section 140 may or may not be hollow.

Although the present invention has been described with reference to preferred embodiments, workers skilled in the art will recognize that changes may be made in form and detail without departing from the spirit and scope of the invention.

The invention claimed is:

1. An occlusion device having first and second occluding bodies and a center connector, the center connector comprising:
   a hollow member connectable to the first occluding body and to the second occluding body; and
   a channel extending though the hollow member defining a plurality of interlocking elements along a generally helical path along a length of the hollow member.

2. The center connector of claim 1 wherein the hollow member comprises a cylinder.

3. The center connector of claim 1 wherein the channel further defines a plurality of interlocking portions.

4. The center connector of claim 3 wherein the interlocking elements comprise a plurality of teeth and grooves.

5. The center connector of claim 4 wherein the interlocking elements further comprise:
   a first number of teeth and grooves positioned around a circumference of a first end of each interlocking portion; and
   a second number of teeth and grooves positioned around a circumference of a second end of each interlocking portion that is not equal to the first number of teeth and grooves.

6. The center connector of claim 3 wherein a number of interlocking portions per length of the hollow member is variable.

7. The center connector of claim 1 wherein a wall of the hollow member comprises a first wall thickness and a second wall thickness that is not equal to the first wall thickness.

8. The center connector of claim 1 wherein the channel defines a gap between the interlocking elements, and the gap varies along a length of the hollow member.

9. The center connector of claim 1 wherein the channel forms the hollow member into a continuous helical band having interlocking elements on one side which interconnect with interlocking elements on an opposite side.

10. The center connector of claim 1 wherein a proximal end of the hollow member is attached to the first occluding body and a distal end of the hollow member is attached to the second occluding body such that the flexible member forms an articulated center connection extending between the first and second occluding bodies.

11. An occlusion device comprising:
    a first occluding body;
    a second occluding body; and
    a center assembly comprising a proximal hub attached to the first occluding body, a a distal hub attached to the second occluding body, and a flexible tubular connector having a proximal end attached to the proximal hub and a distal end attached to the distal hub wherein the flexible tubular connector comprises a plurality of cuts forming interlocking segments which cannot be separated from each other in an axial direction.

12. The occlusion device of claim 11 wherein the interlocking segments of the flexible tubular connector comprise teeth and grooves.

13. The occlusion device of claim 12 wherein the teeth and grooves are formed such that the teeth of one interlocking segment fit into the grooves of an adjacent interlocking segment.

14. The occlusion device of claim 11 wherein the plurality of cuts allows a gap to form between each interlocking segment wherein the interlocking segments can be pushed to remove the gap.

15. The occlusion device of claim 14 wherein the gap has a width which varies along a length of the flexible tubular connector.

16. The occlusion device of claim 11 wherein the number of interlocking segments per unit length of the flexible tubular connector varies along a length of the flexible tubular connector.

17. The occlusion device of claim 11 wherein the flexible tubular connector has a wall thickness which varies along a length of the flexible tubular connector.

18. The occlusion device of claim 11 and further comprising:
    a channel extending through the flexible tubular connector.

19. The occlusion device of claim 18 wherein a width of the channel varies along a length of the flexible tubular connector.

20. The occlusion device of claim 18 wherein the channel defines a continuous helical band comprising a system of teeth and grooves, wherein the teeth located on one side of the band interconnect with the grooves located on an opposite side of the band.

21. The occlusion device of claim 11 wherein the first and second occluding bodies each comprise a collapsible support frame and a sheet attached to the collapsible support frame.

\* \* \* \* \*